(12) United States Patent
Robl et al.

(10) Patent No.: US 8,551,705 B2
(45) Date of Patent: Oct. 8, 2013

(54) USE OF HAPLOID GENOMES FOR GENETIC DIAGNOSIS, MODIFICATION AND MULTIPLICATION

(75) Inventors: James M Robl, Belchertown, MA (US); Pedro Moreira, Sunderland, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 13/015,968

(22) Filed: Jan. 28, 2011

(65) Prior Publication Data

US 2011/0287429 A1    Nov. 24, 2011

Related U.S. Application Data

(63) Continuation of application No. 11/743,613, filed on May 2, 2007, now abandoned, which is a continuation of application No. 10/111,846, filed as application No. PCT/US00/30202 on Nov. 2, 2000, now abandoned.

(60) Provisional application No. 60/163,086, filed on Nov. 2, 1999.

(51) Int. Cl.
*C12Q 1/68*        (2006.01)
*C12N 5/071*       (2010.01)

(52) U.S. Cl.
USPC ............................ 435/6.12; 435/6.1; 435/354

(58) Field of Classification Search
USPC ........................................ 435/6.12, 6.1, 354
See application file for complete search history.

(56) References Cited

U.S. PATENT DOCUMENTS 5,843,780 A * 12/1998 Thomson ...................... 435/363
5,932,418 A *  8/1999 Yager ............................ 435/6.16

OTHER PUBLICATIONS

Johnson et al. Biol. Reprod 41:199-203, 1989.*
Hagemann et al. J Exp Zool 271:57-61, 1995.*
Byrne, (2007), Nature, 450(7169):497-502.
Simerly, (2003), Science, 300(5617):297.
Marshall, (1998), Biol. Reprod., 59:1491-1497.
Hagemann, (1995), J Exp. Zool, 271:57-61.
Johnson, (1989), Biol. Reprod., 41:199-203.
Edirisinghe, (1998), Human Reprod., 13(11):3094-3098.
Barton, (1984), Nature, 311:374-376.
Chan, (1998), PNAS, 95:14028-14033.
Huntriss, (1998), Am. J Hum. Genet, 63:1009-1014.
Harper, (1996),J Assist Reprod. Genet, 13(2):90-95 (Abstract).
Ernst, (1999), J Exp. Zool, 284:112-118.
Ayoub, (1993), J Diary Sci., 76:421-429.
Levron, (1995), Biol. Reprod., 53:209-213.
Modlinski, (1975), J. Embryol., Exp. Morph., 33(4):897-905.
Sims, (1993), PNAS, 90:6143-6147.
Hofmann, (1995), Dev. Genet., 16:119-127.
Henry, (1992), Mole. Reprod. Dev., 31:258-263.
Debec, (1984), Exp. Cell Res., 151:236-246.
Mezger-Freed, (1977), Chromosoma, 1-15.
De Sutter, (1994), J. Assisted Reprod. Genet., 11(8)382-388.
Kaufman, (1983), J. Embryol. Exp. Morph., 73:249-261.
Kono, (1993), Mole. Reprod. Dev., 34:43-46.
Mitalipov, (1999), Biol. Reprod., 60:821-827.
French, (2008), Stem Cells, 26:485-493.
Mitalipov, (2002), Biol. Reprod., 66:1367-1373.
Mitalipov, (2007), Hum. Reprod., 22(8):2232-242.
Vogel, (2003), Science, 300:225-226.
Liu, (2000), Nature Biotech., 18:233-225.
Mitalipov, (2001), Biol. Reprod., 65:253-259.
Wilmut, (2007), Nature, 450:485-486.
Zhao, (2009), Nature, 461:86-92.
Birmingham, (2003), J Clin. Invest., 112:1600-1601.
Boquest, (2002), Biol. Reprod., 66:1283-1287.
Lanza, (2003), Science, 301:1482b.
Strelchenko, (2004), Reprod. BioMed., 9(6):623-629.

* cited by examiner

*Primary Examiner* — Marcia S Noble
(74) *Attorney, Agent, or Firm* — Wolf, Greenfield & Sacks, P.C.

(57) ABSTRACT

Methods for propagating haploid genomes of male or female origina and genetic screening and modification thereof are provided. These haploid genomes may be used to produce haploid embryos, and embryonic stem-like cells and differentiated cells. Also, these haploid genomes and cells containing, may be used as nuclear transfer donors to produce diploid nuclear transfer units. These diploid NT units e.g., human NT units, may be used to obtain pluripotent cells and differentiated cells and tissues.

20 Claims, No Drawings

USE OF HAPLOID GENOMES FOR GENETIC DIAGNOSIS, MODIFICATION AND MULTIPLICATION

CROSS-REFERENCE TO RELATED APPLICATIONS

This application is a continuation of U.S. application Ser. No. 11/743,613, filed May 2, 2007 now abandoned which is a continuation of U.S. application Ser. No. 10/111,846, filed Oct. 3, 2002 now abandoned, which is the National Stage of International Application No. PCT/US00/30202, filed Nov. 2, 2000, which claims the benefit of U.S. Provisional Application No. 60/163,086, filed Nov. 2, 1999. The disclosures of each of the foregoing applications are hereby incorporated by reference in their entirety.

GOVERNMENT RIGHTS

The invention was developed as a result of the expenditure of funds received from the United States Department of Agriculture and accordingly the government has rights to this invention.

FIELD OF THE INVENTION

This invention relates to the propagation and use of haploid genomes for purposes of (1) genetic diagnosis, (2) genetic selection and (3) genetic modification. The selected haploid genomes are useful for the production of embryos and embryonic stem cells when combined with another haploid genome, preferably one having a desired genetic makeup.

BACKGROUND OF THE INVENTION

Gametes are specialized haploid cells (e.g., spermatozoa and oocytes) produced by meiosis and involved in sexual reproduction. By contrast, diploid cell has its chromosomes in homologous pairs, and has two copies of each autosomal genetic locus. The diploid number (2n) equals twice the haploid number and is the characteristic number for most cells other than gametes. A zygote is the diploid cell resulting from the fusion of male and female gametes during fertilization. THE DICTIONARY OF CELL BIOLOGY 103, 139, 388 (J. M. Lackie et al., eds. 1995). Only a (diploid) zygote is capable of giving rise to a viable offspring. By contrast, while haploid gametes conditions may give rise to embryos being parthenogenetic development of female-derived haploid cells (oocytes) these embryos typically stop developing before embryogenesis is completed. Such embryos may be produced spontaneously but more typically are produced by artificial activation of an oocyte. Such gynogenetic embryos are useful for the study of embryogenesis.

The production of properly haploid-derived pluripotent cell lines has previously been reported. For example, purported pluripotent haploid cells were allegedly created by obtaining eggs from 129 SvE or C57BL×CBA hybrid mice and activating them parthenogenetically following exposure to a 7% solution of ethanol in phosphate buffered saline (PBS). However upon examining the chromosomes of these early passage "Haploid" cell lines, all the cells were diploid with a modal number of 40 chromosomes (Kaufman et al., *J. Embryol. Exp. Morphol.* 73: 249-61 (1983)).

While it has been well reported that mammalian embryos may result from haploid genomes, such mammalian embryos have not been used for genetic analysis. Rather, to the best of the inventors' knowledge, prenatal genetic diagnosis is conventionally performed in utero or ex utero using apparent normal (diploid) embryos. However, in utero genetic diagnosis is invasive and can be dangerous to the developing fetus (e.g., amniocentesis and chorionic villi sampling). Fetuses diagnosed with disease can either be aborted or gestated to term, as in utero surgery and gene therapy are still highly risky and experimental.

In humans, ex utero genetic diagnosis is typically performed on embryos produced by in vitro fertilization (IVF) technologies. Typically one or two cells are taken from a recent embryo and tested for such diseases as cystic fibrosis (CF), sex-linked diseases, chromosomal abnormalities, fragile X syndrome, spinal muscular atrophy and myotonic dystrophy (de Die-Smulders et al., *Ned. Tijdschr. Geneeskd.* 142: 2441-4 (1998)). Preimplantation genetic diagnosis (PGD) can be performed using direct polymerase chain reaction (PCR) or nested PCR to diagnose the common $\Delta$F508 mutation of CF (Cui et al., *Mol. Hum. Reprod.* 2: 63-1 (1996); and Ao et al., *Prenat. Diagn.* 16: 137-42 (1996)), as well as other diseases (Ben-Ezra, *Clin. Lab. Med.* 15: 95-815 (1995)). Genetic screening can also be done by single blastomere biopsy for rhesus (RhD) blood group typing of early cleavage stage embryos (Avner et al., *Mol. Hum. Reprod.* 2: 60-2 (1996)) or by blastocyst biopsy (Verlinsky et al., *Bailieres Clin. Obstet. Gynaecol.* 8: 177-96 (1994)). Primed in-situ labeling (PRINS) and in-situ hybridization can be used for detecting human chromosomal abnormalities for PGD (Pellestor et al., *Mol. Hum. Reprod.* 2: 135-8 (1996)). PGD has also been performed using fluorescence in situ hybridization (FISH) to prevent development of moles resulting from a fertilization of an inactive oocyte by a haploid X-bearing spermatozoon, which subsequently duplicates (Reubinoff et al., *Hum. Reprod.* 12: 805-8 (1997)). PGD can be performed on oocytes to diagnose single gene disorders by first polar body analysis and to identify oocytes that contain maternal unaffected genes (Verlinsky et al., *Biochem. Mol. Med.* 62: 182-7 (1997); Verlinsky et al., *Curr. Opin. Obstet. Gynecol.* 4: 720-5 (1992); and Verlinsky et al., *Hum. Reprod.* 5: 826-9 (1990)). In one case, individual spermatoza of a father with two affected infants with osteogenesis imperfecta, were separated by dilution and micromanipulation. A segment of the type I collagen gene containing the mutation was amplified using nested PCR and sequencing to detect the wild-type gene as well as genes with a single point mutation (Iida et al., *Mol. Hum. Reprod.* 2:131-4 (1996)). Methods of selecting sperm have been developed in response to use of intracytoplasmic sperm injection techniques (ICSI) (Meschede et al., *Hum. Reprod.* 10: 2880-6 (1995)). Sequential analysis of first and second polar body and multiplex PCR can lead accurate genetic diagnosis in comparison to the pitfalls encountered by single-cell DNA analysis (Richitsky et al., *J. Assist. Reprod. Genet.* 16: 192-8 (1999)).

Additional methods of genetic screening includes the detection or change in restriction fragment length polymorphisms (RFLPs), variable number of tandem repeat (VNTR) sequences and dinucleotide or other short tandem repeat (STR) sequences. Alternatively, allele specific amplification and allele specific ligation, utilizing primers complimentary to either the wild type or the mutant sequence, provide two alternative means for detection of specific mutations. Other methods are available to screen for the presence of mutations without identifying the specific mutation itself. These methods include single-strand conformational polymorphism (SSCP) analysis, denaturing gradient gel electrophoresis (DGGE), and mismatch cleavage analysis by enzymatic (RNAse A) or chemical (piperidine) means. See Fujimura, "Genetic Testing," IN MOLECULAR BIOLOGY AND BIOTECHNOLOGY: A COMPREHENSIVE DESK REFERENCE 374-379 (Robert A. Meyers, ed., 1995).

Thus, based on the foregoing, it is evident that although research is ongoing in perfecting preimplantation genetic screening, as well as manipulation of embryos created in vitro, little progress has been achieved in the genetic screening of gametes or the genetic manipulation of gametes to be used to make transgenic animals.

Therefore, notwithstanding what has previously been reported in the literature, there exists a need for improved methods of genetic screening of gametes and genetically engineering haploid cells for preparing transgenic animals.

SUMMARY AND OBJECTS OF THE INVENTION

It is an object of the present invention to provide a method for selecting genomes for the production of embryos, embryonic stem cells or embryonic germ cells comprising the steps of: (i) culturing cells containing either a male or female-derived haploid genetic content; (ii) genetically testing the genetic content of said cultured cells to identify whether said haploid genome comprises a genetic defect, a desired gene or lacks a functional gene; and (iii) selecting cells that do not comprise a genetic defect, or selecting cells that contain the desired gene or lack a functional gene.

Specifically, in the case of female-derived haploid cells, the cells can be obtained by one of five methods: (1) by activation of an oocyte in which half of the chromosomes are extruded in the polar body; (2) by fertilization of an egg and removal of a male pronucleus therefrom; (3) by activation of an egg to provide an egg containing two female pronuclei and removal of one of said pronuclei; (4) by insertion of a diploid cell nucleus into an immature oocyte followed by separation of said chromosomes in to two haploid nuclei; and (5) by transfer of the nucleus of a parthenogenetic embryo (contains half the chromosomes) but propagated with the full DNA content (four chromatids) into an oocyte, and subsequent extrusion of half the chromosomes therefrom.

Another object of the invention is directed towards the screening of male-derived haploid cells, which can be obtained by one of the following methods: (1) obtaining the male-derived haploid cell from a fertilized egg from which the female pronucleus is removed; (2) obtaining the male-derived haploid cell by fertilizing an enucleated egg; and (3) obtaining the mal derived haploid cell by artificial decondensation of a sperm nucleus which is then injected into a non-egg derived cytoplast.

Another object of the invention is a method of propagating male- or female-derived haploid cells by a method selected from the group consisting of (i) allowing a haploid egg cytoplast to undergo cell division; (ii) allowing a haploid cell to produce a haploid embryo which is then cultured to produce "propagating haploid" cells; (iii) culturing a haploid embryo to produce embryonic stem-like cells which are haploid and allowing such embryonic stem-like cells to differentiate; and (iv) culturing a haploid somatic cell cytoplast under conditions that allow cell division.

Another object of the invention is to provide a propagated haploid genome cell line of male or female origin, i.e., one which comprises a desired genetic make-up or comprises a desired genetic modification.

Still another object of the invention is to provide pluripotent or embryonic-like stem cells produced from a haploid cell line and differentiated cells derived therefrom, which comprise a desired genetic make-up, e.g., comprise a desired genetic modification.

Yet another object of the invention is to provide diploid mammalian embryos produced from a genetically modified or selected haploid male and/or female genome, as well as pluripotent cell lines and differentiated cells derived therefrom.

DEFINITIONS

The invention relates to the production and multiplication, by any method, of cells containing either a male or female-derived haploid chromosome content, the use of these cells for genetic evaluation, genetic modification or multiplication of a specific haploid genome, and the use of these cells in producing an embryo with a diploid content of DNA. The haploid genomes to be propagated, screened and/or modified include ungulates, such as bovine, ovine, porcine, equine, caprine; canine, feline, murine, rabbit, and rodents (e.g., guinea pigs, hamsters and rats), human, non-human primates, such as cynomolgus monkey, chimpanzees, baboon and gorilla.

By "genetic screening," "genetic diagnosis," "genetic analysis" and "genetic testing" is meant the analysis of the haploid genome by conventional methods to detect the presence or absence of a specific DNA associated with a phenotype, disease or condition. Such methods include in situ hybridization, polymerase chain reaction, nested polymerase chain reaction, fluorometric detection methods, RFLP analysis VNTR or STR detection methods (which screen for usage in a number of tandem repeat dinucleotide or other short tandem repeat (STR) sequences, single-strand conformational polymorphism (SSCP) analysis, denoting gradient gel electrophoresis (DGGE) and mismatch cleavage analysis i.e., by enzymatic (RNAse A) or chemical (piperidine) means. Such methods are reviewed in Fujimura "Genetic Testing", IN MOLECULAR BIOLOGY AND BIOTECHNOLOGY: A COMPREHENSIVE DESK REFERENCE 374-379 (Robert A. Meyers, ed., 1995).

By "genetic selection" is meant the directed choice of a genotype using genetic testing.

By "genetic modification" or "genetic manipulation" is meant the modification of the genome of a cell, typically a haploid cell. This includes insertion, deletion and substitute modifications. Preferably the modification will be effected at a target site in the genome. In a preferred embodiment, the modified haploid cell will eventually be used in nuclear transplantation for production of an animal which expresses the modified/manipulated gene.

By "multiplication" is meant increasing the number of cells comprising the desired haploid genome of male or female origin.

By "haploid cell" is meant a cell with a haploid number (n) of chromosomes. "Gametes" are specialized haploid cells (e.g., spermatozoa and oocytes) produced by meiosis and involved in sexual reproduction. A "diploid cell" has its chromosomes in homologous pairs, and has two copies (2n) of each autosomal genetic locus. A "zygote" is the diploid cell resulting from the fusion of a male and a female gamete during fertilization.

The term "nuclear transfer" or "nuclear transplantation" refers to a method of cloning wherein the nucleus from a donor cell is transplanted into an enucleated oocyte. Nuclear transfer techniques or nuclear transplantation techniques are known in the literature (Campbell et al., *Theriogenology* 43: 181 (1995); Collas et al., *Mol. Reprod. Dev.* 38: 264-267 (1994); Keefer et al., *Biol. Reprod.* 50: 935-939 (1994); Sims et al., *Proc. Natl. Acad. Sci. USA* 90: 6143-6147 (1993); Evans et al., WO 90/03432 (5 Apr. 1990); Smith et al., WO 94/24274 (27 Oct. 1994); Wheeler et al., WO 94/26884 (24 Nov. 1994)). Also, U.S. Pat. Nos. 4,994,384 and 5,057,420 describe procedures for bovine nuclear transplantation. See also U.S. Pat. No. 5,945,577; WO 97/06668 and WO 97/06669, which respectively name The University of Massachusetts and Roslin Institute as the Assignee or Applicant. This patent and applications are incorporated by reference herein. In the subject application, nuclear transfer or nuclear transplantation or NT are used interchangeably. The present definition also embraces the implantation of one or two selected haploid genomes to produce an embryo.

By "lack a functional gene" is meant either the entire gene is missing from the subjects genome, or the gene is mutated to an extent that it can no longer function (e.g., produce a wild-type protein).

By "genetic defect" is meant a nucleic acid deletion or insertion which corresponds to an alteration in transcription of the gene, translation of the gene's mRNA into a protein, alteration of the half-life of the protein or the gene's mRNA or other change from wild-type expression of the gene. Different forms of a given gene are called "alleles." The "wild-type alleles" of a gene are those that exist at relatively high frequencies in natural populations and yield wild-type or normal phenotypes. Alleles of a gene that result in abnormal or non-wild-type phenotypes are "mutant alleles."

By "propagating haploid cell line" is meant a cell line of proliferating haploid cells produced artificially outside of the haploid cell's host organism. Typically such haploid cell line will be comprised in an in vitro culture. Alternatively, a haploid cell may be propagated in vivo, e.g. by injection into a SKID mouse to produce differentiated cell types.

DETAILED DESCRIPTION OF THE INVENTION

As discussed, the present invention is directed toward the production and propagation of haploid genomes, the selection of desirable haploid genomes from said propagated haploid genomes by genetic analysis, and the use of said selected haploid genomes to produce diploid embryos. As noted in the background of this application, it is known to conduct genetic evaluation of preimplantation embryos as a means of selecting embryos suitable for implantation and the production of offspring. Such methods involve genetic evaluation of the genome of one or more cells of the embryo prior to implantation.

However, such methods may pose ethical issues in that an embryo is manipulated, and potentially may be destroyed if it exhibits undesirable genetic characteristics. Most especially, such methods may pose ethical issues in the context of human preimplantation embryos, especially those produced by nuclear transfer or conventional in vitro fertilization.

By contrast, the present invention selects haploid DNA for use in the production of diploid embryos by genetic testing of a haploid cell genome. Such methods should not pose the same ethical concerns as haploid cells cannot give rise to viable offspring.

Thus, the disposal of non-desirable haploid genomes or manipulation of haploid genomes should obviate ethical issues associated with manipulation and destruction of diploid embryos, e.g. human diploid embryos.

Because the present invention involves genetic testing of haploid genomes, it requires a propagated source of such haploid genome. This initially entails constructing or obtaining a cell containing a haploid genome, and providing for proliferation thereof.

Various methods for producing cells containing either male or female haploid genomes may be utilized. For example, methods of producing haploid cells containing haploid genomes of female origin include by way of example:

(i) activating in vitro an oocyte in which half the chromosomes are extruded in the polar body;

(ii) fertilizing an egg and removal of the male pronucleus;

(iii) activating in vitro an egg which comprises two female pronuclear and removal of one of said pronuclear therefrom;

(iv) insertion of a diploid cell nucleus into an immature oocyte and separation of the chromosomes into two haploid nuclei and (v) transfer of a parthenogenetic nucleus (which contains half the number of chromosomes) but is propagated with the full DNA content (four chromotides) into an oocyte and half the chromatides are extruded therefrom.

Of the above methods (i), (iii), (iv) and (v) are preferred, as the methods at no time result in a diploid embryo wherein half its DNA content is of male and the other half is of female origin. Thus, even if implanted, they would be incapable of developing into a full-term offspring.

Methods for providing haploid genomes of male origin include:

(i) fertilization of an egg and removal of the female pronucleus;

(ii) fertilization of a enucleated oocyte; and (iii) artificial decondensation of a sperm nucleus and injection into a non egg-derived cytoplast.

The above-described haploid cells and other haploid cells may be propagated by various methods. For example, haploid genomes may be propagated by inducing division of egg cytoplasts. Alternatively, haploid embryos may be used for the product of embryonic stem-like cells. This may be effected by culturing the embryo using known media and methods for maintaining embryos in culture and culturing the inner cell mass or cells derived therefrom to produce embryonic stem-like cells. For example, this may be effected by placing the inner cell mass or cells of the inner cell mass of a haploid-genome derived embryo on a feeder layer, e.g. murine fetal fibroblasts, to produce a culture containing embryonic stem-like cells which give rise to different differentiated cell types, e.g., when removed from the feeder layer.

Still alternatively, embryonic stem-like cells derived from haploid embryos may be used to produce differentiated cells which have the genome of the parent haploid genome. Yet another means of propagating haploid genomes comprises inducing division of haploid somatic cell cytoplasts produced by introduction of a haploid genome into a cytoplast.

As noted, in its preferred embodiment the haploid genome will be of human origin, e.g. that of human sperm, or oocyte. However, the present invention embraces the construction of haploid genomes of any mammalian species origin, e.g. non-human primate, dog, cat, mouse, rat, rabbit, bear, cow, horse, pig, sheep, guinea pig, buffalo, goat, antelope, etc. Essentially, the invention is applicable for the selection of any animal that is desirably propagated, e.g. by nuclear transfer, that contains a desired genetic makeup of particular importance are agricultural animals, especially animals having a long gestation period. The present invention should enable rapid screening for haploid genomes that will give rise to diploid embryos having desired genetic characteristics. For example, the presence or absence of sex-linked genetic diseases can be the basis of the genetic screen.

Also, the invention allows for haploid cell line produced according to the invention to be genetically modified, by homologous recombination.

This is an advantageous aspect of the invention because allelic differences at a locus will not interfere with the desired recombination events. Also, the present invention allows for the same locus to be targeted in both the male and female haploid cell lines, and the resultant modified male and female haploid genomes to be combined to produce a diploid embryo that is homozygous for the particular modification, e.g. deletion of a particular gene.

As discussed, the invention described herein improves upon prior methods of preimplantation genetic diagnosis (PGD), because these methods do not involve the manipulation of an embryo. Generally, few embryos are available for screening. Moreover, removal of the cells from an embryo for testing can be harmful for further development of the embryo. Often only one or very few cells are available for genetic testing, which can lead to inaccurate results due to DNA loss or DNA contamination. Finally, there are ethical considerations regarding embryo disposal. Genetic screening of haploid DNA offers the advantage that if male and/or female gametes are screened then, even with few gametes, the total possible combination becomes large.

In the case of sex-linked genetic diseases, screening can be done on sperm only, which is typically easy to obtain in large quantities. If the sperm is not available in large quantities, then multiplication of the sperm genome can also be useful. The technique makes many identical copies of the genome available for screening to minimize the likelihood of misdiagnosis, and permits additional samples to be analyzed for verification of results. The ethical concerns about working with and manipulating sperm are minimal in comparison with those for working with embryos.

Screening of haploid cells can also be performed e.g., to determine whether genetic or DNA methylation defects in the haploid cell may cause any adult animal developed therefrom to contract cancer or other disease. Screening for genetic conditions and predispositions would be useful in eliminating defective haploid cells containing such defects. The present invention can be used to screen for chromosomal aberrations and DNA sequences that are correlated to disease or other undesirable traits. These haploid genomes will typically be disposed of. However, in some instances such haploid genomes may be retained. For example, the production of haploid genomes that encode genes that are involved in disease may be useful in producing animals for research purposes, e.g. for evaluating the efficacy of putative therapeutics or prophylactics. Also, the present invention can be used to select haploid genomes that contain a desired genetic makeup, e.g., comprise DNA sequences that are involved in enhanced growth, disease resistance, milk production, or other desirable traits. For example, genetic analysis of haploid cells using DNA probes and linkage (L) or mutation (M) detection can be made on the following human diseases listed in Table 1:

TABLE 1

| Condition | Chromosome | L/M | Cloned |
| --- | --- | --- | --- |
| α-1 antitrypsin deficiency | 14 | M | Yes |
| α-Thallasemia | 16 | M | Yes |
| Adenomatous polyposis coli | 5 | L, M | Yes |
| Adult polycystic kidney disease | 16 | L | No |
| Breast cancer susceptibility (BRCA1) | 17 | L, M | Yes |
| Breast cancer susceptibility (BRCA2) | 13 | L | No |
| β-Thallasemia | 11 | M | Yes |
| Charcot-Marie-Tooth disease | 1 | M | Yes |
| Colon cancer susceptibility (MSH2) | 2 | M | Yes |
| Colon cancer susceptibility (MLH1) | 3 | M | Yes |

TABLE 1-continued

| Condition | Chromosome | L/M | Cloned |
| --- | --- | --- | --- |
| Colon cancer susceptibility (PMS1) | 2 | M | Yes |
| Colon cancer susceptibility (PMS2) | 7 | M | Yes |
| Congenital adrenal hyperplasia | 6 | M, L | Yes |
| Cystic Fibrosis (CF) | 7 | M | Yes |
| Duchenne/Becker muscular dystrophy | X | M, L | Yes |
| Fragile X syndrome | X | M, L | Yes |
| Hemophilia A | X | M, L | Yes |
| Gaucher's disease | 1 | M | Yes |
| Hemophilia B | X | M, L | Yes |
| Huntington's disease | 4 | M, L | Yes |
| Kennedy's disease | X | M | Yes |
| Lesch-Nyhan syndrome | X | L, M | Yes |
| Marfan's syndrome | 15 | M | Yes |
| Medium chain acyl-coenzyme A dehydrogenase deficiency | 1 | M | Yes |
| Melanoma susceptibility | 9 | M | Yes |
| Multiple endocrine neoplasia 1 | 11 | L | No |
| Multiple endocrine neoplasia 2A | 10 | L, M | Yes |
| Myotonic dystrophy | 19 | M, L | Yes |
| Neurofibromatosis type 1 | 17 | L, M | Yes |
| Ornithine transcarbamylase deficiency | X | M, L | Yes |
| Retinoblastoma | 13 | M, L | Yes |
| Sickle cell anemia | 11 | M | Yes |
| Steroid sulfatase deficiency | X | L, M | Yes |
| Tay-Sachs disease | 15 | M | Yes |
| Werdnig-Hoffman disease | 5 | L | No |

Frank K. Fujimura, "Genetic Testing," IN MOLECULAR BIOLOGY AND BIOTECHNOLOGY: A COMPREHENSIVE DESK REFERENCE (Robert A. Meyers, ed. 1995).

Methods for screening genomes for the presence of specific DNA sequences or chromosomal aberrations are well known. Such screening methods include by way of example polymerase chain analysis (PCR) techniques including nested PCR and direct PCR amplification, SSCP analysis, RFLP analysis, primed in situ labeling (PRINS) methods (see Pellestor et al., 1996), fluorescence in situ hybridization (FISH) analysis, and analysis of VNTRs or STRs, denaturing gradient gel electrophoresis (DGGE), and mismatch cleavage analysis using enzymatic RNAse A) or chemical (e.g., piperidine) methods.

Other screening methods include DNA methylation analysis which is useful for identifying syndromes associated with genomic imprinting. Syndromes and diseases in humans associated with genomic imprinting include: Prader-Willi syndrome (PWS), Angelman syndrome (AS), uniparental isodisomy, Beckwith-Wiedermann syndrome (BWS), Wilm's tumor carcinogenesis and von Hippel-Lindau (VHL) disease. For methods of performing DNA methylation analysis, see Buchholz et al., Hum. Genet. 103: 535-9 (1998). PWS can be caused by genetic mutations, such as deletions, as well as abnormal genomic imprinting (Barabash et al., Med. Clin. (Barc) 108: 304-6 (1997)). In animals, genomic imprinting has also been linked to coat color. For example, the mouse agouti gene confers wild-type coat color, and differential expression of the Aiapy allele correlates with the methylation status of the gene's upstream regulatory sequences (Michaud et al., Genes Dev. 8: 1463-72). Genetic screening in agriculture can be used for genetic selection to produce optimal combinations that minimize recessive mutations, increases heterozygosity or homozygosity or to accumulate beneficial or otherwise desired alleles.

As noted above, many genetic screening and testing methods are known in the art and may be used in the present invention. Also, many sequences have been identified that correlate to desired or undesired traits.

The methods of the present invention can be used for genetic selection, both in animals, e.g., agricultural, laboratory or domestic animals as well as in humans. Currently, the combination of gamete genomes that constitute the embryo is random. However, by performing genetic screening on gametes, the optimal combinations could be made to minimize recessive mutations, increase heterozygosity, increase homozygosity or accumulate beneficial alleles. Haploid genomes that are selected to have desirable genetic makeup would be used to provide diploid embryos and offspring.

As further discussed, the methods of producing propagating haploid cells can also be used to prepare genetically modified haploid cells. In the cases of homologous recombination, allelic differences at a locus will not interfere with the recombination event. Furthermore, targeting both male and female cell lines can result in the preparation of homozygous modifications.

Methods for effecting genomic modification are well known in the art and include by way of example the use of retroviral vectors, microinjection, and transformation with DNAs comprising sequences that are to be inserted. Preferably, the genetic modification will be made at a targeted site in the genome. Methods for effecting targeted insertion, deletion and substitute modifications of genomes, and particularly mammalian genomes have been well reported and are the subject of numerous patents.

Essentially, in the present invention a particular haploid genome contained in a propagated haploid cell line will be genetically modified in order to remove, add or substitute a particular DNA sequence with another. After such genetic modification has been effected, e.g. by homologous recombination, the haploid genome will be tested or screened to determine that it indeed comprises the modification. For example, this can be effected by one of the genetic screening methods identified supra, or by expression of a particular marker contained in the inserted DNA, e.g., enzyme, antibiotic resistance marker, fluorescent or radiolabel, etc.

After the genetically modified haploid genome has been produced, it preferably will be amplified by the methods discussed previously.

The resultant selected haploid of male or female origin, genomes which may be genetically modified, are especially useful for nuclear transfer or transplantation. Essentially, such methods will comprise the introduction of a selected male and female haploid genome into an enucleated oocyte, or the introduction of a selected male or female haploid genome into a haploid oocyte wherein such haploid DNA is either of male or female origin. Thereby, diploid nuclear transfer unit will be obtained, wherein either or both the male or female DNA therein has been selected based on its genetic makeup. Those diploid nuclear transit units can be used to provide progeny that have a desired genetic makeup, e.g., contain genes involved in disease resistance, growth, or a heterologous DNA that encodes a desired product.

Nuclear transfer techniques or nuclear transplantation techniques are well known in the literature. See, in particular, Sims et al., *Proc. Natl. Acad. Sci. USA* 90: 6143-6147 (1993); Collas et al., *Mol. Report. Dev.* 38: 264-267 (1994); Keefer et al., *Biol. Reprod.* 50: 935-939 (1994); Campbell et al., *Theriogenology*, 43: 181 (1995); Campbell et al., *Nature*, 380: 64-66 (1996); Schnieke et al., *Science* 278: 2130-3 (1997); Wells et al., *Biol. Reprod.* 57: 385-393 (1997); Wilmut et al., *Nature* 386: 810-813 (1997); Cibelli et al., *Science* 280: 1256-8 (1998); Kato et al., *Science* 282: 2095-8 (1998); Wakayama et al., *Nature* 394: 369-74 (1998); Wolf et al., *J. Biotechnol.* 65: 99-110 (1998); Baguisi et al., *Nat. Biotechnol.* 17: 456-61 (1999); Dominko et al., *Biol. Reprod.* 60: 1496-1502 (1999); Wolf et al., *Biol. Reprod.* 60: 199-204 (1999); PCT/US99/00045; WO 94/26884; WO 94/24274; and WO 90/03432, which are herein incorporated by reference in their entirety. Also, U.S. Pat. Nos. 4,944,384 and 5,057,420 describe procedures for bovine nuclear transplantation. See also, U.S. Pat. No. 5,945,577, incorporated by reference in its entirety.

Oocytes used for nuclear transfer may be obtained from animals including mammals and amphibians. Suitable mammalian sources for oocytes include sheep, bovines, ovines, pigs, horses, rabbits, guinea pigs, mice, hamsters, rats, primates, human and non-human etc. In the preferred embodiments, the oocytes will be obtained from primates, e.g., human oocytes, or ungulates.

Methods for isolation of oocytes are well known in the art. Essentially, this will comprise isolating oocytes from the ovaries or reproductive tract of a mammal, e.g., a bovine. A readily available source of bovine oocytes is from slaughterhouse materials.

For the successful use of techniques such as genetic engineering, nuclear transfer and cloning, oocytes must typically are matured in vitro before these cells may be used as recipient cells for nuclear transfer, and before they can be fertilized by the sperm cell to develop into an embryo. This process generally requires collecting immature (prophase I) oocytes from ovaries (e.g., bovine ovaries obtained at a slaughterhouse) and maturing the oocytes in a maturation medium prior to fertilization or enucleation until the oocyte attains the metaphase II stage, which in the case of bovine oocytes generally occurs about 18-24 hours post-aspiration. For purposes of the present invention, this period of time is known as the "maturation period." As used herein for calculation of time periods, "aspiration" refers to aspiration of the immature oocyte from ovarian follicles. Also, the invention includes the isolation of human oocytes by aspiration from consenting donors.

Alternatively, metaphase II stage oocytes, which have been matured in vivo can be used in nuclear transfer techniques. For example, mature metaphase II oocytes are collected surgically from either non-superovulated or superovulated cows or heifers 35 to 48 hours past the onset of estrus or past the injection of human chorionic gonadotropin (hCG) or similar hormones.

The stage of maturation of the oocyte at enucleation and nuclear transfer has been reported to be significant to the success of NT methods. (See e.g., Prather et al., *Differentiation* 48: 1-8 (1991); Tanaka et al., *Anim. Reprod. Sci.* 49: 113-23 (1997)). In general, successful mammalian embryo cloning practices use metaphase II stage oocytes as recipient oocytes, because at this stage it is believed that the oocyte can be or is sufficiently "activated" to treat the introduced nucleus as it would a fertilizing sperm. In domestic animals, and especially cattle, the oocyte activation period generally ranges from about 16-52 hours, preferably about 28-42 hours post-aspiration.

For example, immature oocytes may be washed in HEPES buffered hamster embryo culture medium (HECM) as described in Seshagine et al., *Biol. Reprod.* 40: 544-606 (1989), and then placed into drops of maturation medium consisting of 50 µl of tissue culture medium (TCM) 199 containing 10% fetal calf serum (FCS), which contains appropriate gonadotropins such as luteinizing hormone (LH) and follicle stimulating hormone (FSH), and estradiol under a layer of lightweight paraffin or silicon at 39° C.

After a fixed maturation period, which ranges from about 10 to 40 hours, and preferably about 16-18 hours, oocytes can be enucleated. Prior to enucleation the oocytes are preferably removed and placed in HECM containing 1 mg/ml of hyaluronidase prior to removal of cumulus cells. This may be effected by either repeated pipetting through very fine bore pipettes or by vortexing briefly. The stripped oocytes are then screened for polar bodies, and the selected metaphase II oocytes, as determined by the presence of polar bodies, are then used for nuclear transfer. Enucleation follows.

Enucleation may be effected by known methods, such as described in U.S. Pat. No. 4,994,384, which is herein incorporated by reference. For example, metaphase II oocytes are either placed in HECM, optionally containing 7.5 μg/ml cytochalasin B, for immediate enucleation, or may be placed in a suitable medium, for example CR1aa, plus 10% estrus cow serum, and then enucleated later, preferably not more than 24 hours later, and more preferably 16 to 18 hours later.

Enucleation may be accomplished microsurgically using a micropipette to remove the polar body and the adjacent cytoplasm. The oocytes may then be screened to identify those of which have been successfully enucleated. This screening may be effected by staining the oocytes with 1 μg/ml 33342 Hoechst dye in HECM, and then viewing the oocytes under ultraviolet irradiation for less than 10 seconds. The oocytes that have been successfully enucleated then can be placed in a suitable culture medium, e.g., CR1aa plus 10% serum.

In the present invention, one or two selected, potentially genetically modified haploid genomes will be transplanted into a perivitelline space of an optionally enucleated oocyte or other cytoplast. The resultant haploid genome containing oocyte or cytoplast which is diploid is used to produce NT units according to methods known in the art. For example, the cells may be fused by electrofusion. Electrofusion is accomplished by providing a pulse of electricity that is sufficient to cause a transient breakdown of the plasma membrane. This breakdown of the plasma membrane is very short because the membrane reforms rapidly. Essentially, if two adjacent membranes are induced to breakdown and upon reformation the lipid bilayers intermingle, small channels will open between the two cells. Due to the thermodynamic instability of such a small opening, it enlarges until the two cells become one. Reference is made to U.S. Pat. No. 4,997,384 by Prather et al., for a further discussion of this process. A variety of electrofusion media can be used including, e.g., sucrose, mannitol, sorbitol and phosphate buffered solution. Fusion can also be accomplished using Sendai virus as a fusogenic agent (Graham, *Wister Inst. Symp. Monogr.* 9: 19 (1969)

Also, in some cases (e.g., with small donor nuclei) it may be preferable to inject the haploid cell or nucleus directly into the oocyte rather than using electroporation fusion. Such techniques are disclosed in Collas et al., *Mol. Reprod. Dev.* 38: 264-267 (1994).

Human or animal cells and oocytes or cytoplasts can be electrofused by known methods, e.g., in a 500 μm chamber by application of an electrical pulse of 90-120 V for about 15 μsec, about 24 hours after initiation of oocyte maturation. After fusion, the resultant fused NT units are then placed in a suitable medium until activation. Activation can be effected shortly before or after fusion, typically less than 24 hours later, and preferably about 4-9 hours later.

The NT unit may be activated by known methods. Such methods include, e.g., culturing the NT unit at sub-physiological temperature, in essence by applying a cold, or actually cool temperature shock to the NT unit. This may be most conveniently done by culturing the NT unit at room temperature, which is cold relative to the physiological temperature conditions to which embryos are normally exposed.

Alternatively, activation may be achieved by application of known activation agents. For example, penetration of oocytes by sperm during fertilization has been shown to activate prefusion oocytes to yield greater numbers of viable pregnancies and multiple genetically identical calves after nuclear transfer. Also, treatments such as electrical and chemical shock may be used to activate NT embryos after fusion. Oocyte activation methods are the subject of U.S. Pat. No. 5,496,720, to Susko-Parrish et al.

Additionally, activation may be affected by simultaneously or sequentially:
(i) increasing levels of divalent cations in the oocyte, and
(ii) reducing phosphorylation of cellular proteins in the oocyte.

This will generally be affected by introducing divalent cations into the oocyte cytoplasm, e.g., magnesium, strontium, barium or calcium, e.g., in the form of an ionophore. Other methods of increasing divalent cation levels include the use of electric shock, treatment with ethanol and treatment with caged chelators.

Phosphorylation may be reduced by known methods, e.g., by the addition of kinase inhibitors, such as serine-threonine kinase inhibitors (e.g., 6-dimethylamino-purine, staurosporine, 2-aminopurine, and sphingosine). Alternatively, phosphorylation of cellular proteins may be inhibited by introduction of a phosphatase into the oocyte (e.g., phosphatase 2A and phosphatase 2B).

One means of effecting NT activation is by briefly exposing the fused NT unit to a TL-HEPES medium containing 5 μM ionomycin and 1 mg/ml BSA, followed by washing in TL-HEPES containing 30 mg/ml BSA within about 24 hours after fusion, and preferably about 4 to 9 hours after fusion. Alternatively, activation can be effected by use of ethanol or repeated electrical pulse.

The activated NT units produced from one or two selected haploid genomes may then be cultured in a suitable in vitro culture medium until the generation of embryonic or stem-like cells and cell colonies. Culture media suitable for culturing and maturation of embryos are well known in the art. Examples of known media, which may be used for bovine embryo culture and maintenance, include Ham's F-10+10% fetal calf serum (FCS), Tissue Culture Medium-199 (TCM-199)+10% fetal calf serum, Tyrodes-Albumin-Lactate-Pyruvate (TALP), Dulbecco's Phosphate Buffered Saline (PBS), Eagle's and Whitten's media. One of the most common media used for the collection and maturation of oocytes TCM-199 plus an 1 to 20% serum supplement, including fetal calf serum, newborn serum, estrual cow serum, lamb serum or steer serum. A preferred maintenance medium includes TCM-199 with Earl salts, 10% fetal calf serum, 0.2 mM Na pyruvate and 50 μg/ml gentamicin sulphate. Any of the above may also involve co-culture with a variety of cell types such as granulosa cells, oviduct cells, BRL cells, uterine cells and STO cells.

Afterward, activation of the cultured NT unit or units are preferably washed and then placed in a suitable media, e.g., CRIaa medium containing 10% FCS and 6 mg/ml contained in well plates which preferably contain a suitable confluent feeder layer. Suitable feeder layers include, by way of example, fibroblasts and epithelial cells, e.g., fibroblasts and uterine epithelial cells derived from ungulates, chicken fibroblasts, murine (e.g., mouse or rat) fibroblasts, STO and SIm220 feeder cell lines, and BRL cells.

The NT units are cultured on the feeder layer until the NT units reach a size suitable for obtaining cells which may be used to produce embryonic stem-like cells or cell colonies. Preferably, these NT units will be cultured until at least about 2 to 400 cells, more preferably about 4 to 128 cells, and most preferably at least about 50 cells. The culturing will be effected under suitable conditions, e.g., about 38.5° C. and 5% $CO_2$, with the culture medium changed in order to optimize growth typically about every 2-5 days, preferably about every 3 days.

After NT units of the desired size are obtained, the cells are mechanically removed from the zone and are then used to produce embryonic or stem-like cells and cell lines. This is preferably effected by taking the clump of cells which comprise the NT unit, which typically will contain at least about 50 cells, washing such cells, and plating the cells onto a feeder layer, e.g., irradiated fibroblast cells. Typically, the cells used to obtain the stem-like cells or cell colonies will be obtained from the inner most portion of the cultured NT unit, which is preferably at least 50 cells in size. However, NT units of smaller or greater cell numbers, as well as cells from other portions of the NT unit, may also be used to obtain ES-like cells and cell colonies. The cells are maintained in the feeder layer in a suitable growth medium, e.g., alpha MEM supplemented with 10% FCS and 0.1 mM β-mercaptoethanol (Sigma) and L-glutamine. The growth medium is changed as often as necessary to optimize growth, e.g., about every 2-3 days. This culturing process results in the formation of embryonic or stem-like cells or cell lines. The culture time before such cells are produced may vary dependent upon the particular nuclear donor cell, specific oocyte and culturing conditions. One skilled in the art can vary the culturing conditions as desired to optimize growth of the particular embryonic or stem-like cells.

The embryonic or stem-like cells and cell colonies produced from said haploid genome generated embryos should exhibit an appearance similar to native embryonic or stem-like cells of the species used as the nuclear cell donor.

The present invention has been described with reference to a preferred embodiment. However, it will be readily apparent to those skilled in the art that it is possible to embody the invention in specific forms other than as described above without departing from the spirit of the invention. The preferred embodiments described in the examples below are illustrative and should not be considered restrictive in any way. The scope of the invention is given by the appended claims, rather than the preceding description, and all variations and equivalents which fall within the range of the claims are intended to be embraced therein.

Example

Production of a Haploid Cell Line

Production of Large Murine A9 Cells

Murine A9 cells (HPRT-) are cultured in 3.75 µg/ml cytochalasin B (Sigma, location) in alphamem (Biowhittaker, location) supplemented with 10% fetal bovine serum for 96 hrs. Cytochalasin B is an inhibitor of microfilaments and will prevent the cells from undergoing cytokinesis while allowing the cell to synthesize DNA and increase in size. After 24 hrs recovery from the drug, cells can be removed from the culture surface and manipulated. Resulting cells are approximately 30 µm in diameter.

Education

Round glass discs, approximately 2.5 cm in diameter are coated with poly-D-lysine. Cytochalasin B treated A9 cells are plated at 60-80% confluency on the discs and allowed to adhere for 24 hrs. Discs are placed cell-side down in centrifuge tubes containing 5 ml enucleation medium (phosphate buffered saline, 10% fetal bovine serum, 10 µg/ml cytochalasin B). Cells are incubated for 20 min at 37° C. Centrifuge tubes are placed in 37° C. ultracentrifuge and spun at 23,000 g for an additional 20 min. Resulting cytoplasts are viable for 24-48 hrs.

Cytoplasts are removed from the glass surface by trypsinization. HAT supplement is added to culture medium at 1× concentration to kill remaining nucleated cells. An alternative to this is to add the HAT supplement following introduction of the donor nucleus. This will eliminate any nucleated A9 cells while any unfused cytoplasts will lyse within 48 hrs.

Introduction of Donor Nucleus

Sperm collected from transgenic mice, carrying the neomycin resistance gene (Neo), are prepared for fusion by either capacitation or treatment with protease. These treatments are used to ensure that the sperm will stick to the cytoplasts. Transgenic markers are useful for verifying the source of the sperm but are not necessary for the procedure. Alternative haploid donors are the male and female pronuclei (haploid karyoplasts) removed from newly fertilized embryos by micromanipulation.

Fusion

Both the A9 cytoplasts and sperm are treated with protease or with PHA to increase the likelihood of cytoplast to sperm adhesion and fusion. The appropriate concentration of sperm or donor nuclei and cytoplasts should be used to enhance the number of resulting cells with a single nucleus. An AC pulse can be used to orient nuclear/cytoplast couplets so that the membranes to be fused are perpendicular to the flow of current. A DC pulse will be administered to induce fusion between the nuclear donor cell and the cytoplast. Other methods of cell fusion could also be used in the procedure such as polyethylene glycol, fusion-inducing viruses or liposomes.

Selection

Several days following fusion, selection for A9-haploid nuclear hybrids will be started. HAT sensitive A9 cells will be used as a source of cytoplasts, therefore, any colonies that form in the HAT medium will be from haploid-cytoplast hybrids. Non enucleated A9 cells will not survive selection. Resulting hybrids will be clonally propagated until there are sufficient numbers to analyze. We will determine whether hybrids are haploid or diploid by fluorescent in situ hybridization or karyotyping.

Fertilization

Haploid cells can be used as donor nuclei in the fertilization of oocytes. Nuclear transfer is effected using standard procedures. Embryos will be activated using a method that results in second polar body extrusion and haploidization of the female chromatin.

What is claimed is:

1. A method for selecting an animal cell comprising a haploid genome, comprising the following steps:
   (i) producing an animal embryo comprising a haploid genome of male or female origin;
   (ii) culturing said embryo to produce a multi-celled embryo comprising a haploid genome of male or female origin;
   (iii) isolating one or more cells from said multi-celled embryo and screening said one or more cells for a desired genetic makeup; and
   (iv) selecting one or more cells determined to comprise the desired genetic makeup.

2. A method for producing an animal embryo having a desired genetic makeup, the method comprising:
   (i) producing an animal embryo comprising a haploid genome of male or female origin;
   (ii) culturing said embryo to produce a multi-celled embryo comprising a haploid genome of male or female origin;
   (iii) isolating one or more cells from said multi-celled embryo and screening said one or more cells for a desired genetic makeup;

(iv) selecting said one or more cells determined to comprise the desired genetic makeup; and
(v) transferring the nucleus of said one or more cells selected in step (iv) into an oocyte and activating said oocyte to produce an embryo comprising said desired genetic makeup.

3. The method of claim 2, wherein said oocyte is an enucleated oocyte or a haploid oocyte.

4. The method of claim 3, further comprising introducing a second haploid genome into said enucleated oocyte.

5. The method of claim 3, wherein said haploid oocyte comprises a haploid genome having a desired genetic makeup.

6. A method for producing an animal embryonic stem cell having a desired genetic makeup, the method comprising:
(i) producing an animal embryo comprising a haploid genome of male or female origin;
(ii) culturing said embryo to produce a multi-celled embryo comprising a haploid genome of male or female origin;
(iii) isolating one or more cells from said multi-celled embryo and screening said one or more cells for a desired genetic makeup;
(iv) selecting said one or more cells determined to comprise the desired genetic makeup;
(v) transferring the nucleus of said one or more cells selected in step (iv) into an oocyte and activating said oocyte to produce an embryo comprising said desired genetic makeup;
(vi) culturing said embryo comprising a desired genetic makeup produced in step (v) to a stage where the embryo comprises a discernible inner cell mass; and
(vii) isolating said inner cell mass and culturing said inner cell mass, thereby producing embryonic stem cells comprising a haploid genome of male or female origin.

7. The method of claim 2, wherein said animal embryo is produced by activation of an oocyte in which half of the chromosomes are extruded in the polar body.

8. The method of claim 2, wherein said animal embryo is produced by fertilization of an oocyte and removal of a male pronucleus therefrom.

9. The method of claim 2, wherein said animal embryo is produced by activation of an oocyte to provide an oocyte containing two female pronuclei, and removal of one of said pronuclei.

10. The method of claim 2, wherein said animal embryo is produced by insertion of a diploid cell nucleus into an immature oocyte followed by separation of said chromosomes into two haploid nuclei.

11. The method of claim 2, wherein said animal embryo is produced by transfer of the nucleus of a parthenogenetic cell into an enucleated oocyte.

12. The method of claim 2, wherein said animal embryo is derived from a fertilized oocyte from which the female pronucleus is removed.

13. The method of claim 2, wherein the animal embryo is derived by fertilization of an enucleated oocyte.

14. The method of claim 2, wherein the animal embryo is produced by artificial de-condensation of a sperm nucleus which is then injected into a non-oocyte derived cytoplast.

15. The method of claim 2, wherein said animal embryo is human.

16. The method of claim 3, wherein said oocyte is a haploid oocyte and wherein said embryo comprising said desired genetic makeup is diploid.

17. The method of claim 2, wherein said haploid genome is genetically modified.

18. The method of claim 1, wherein said screening said one or more cells for a desired genetic makeup in step (iii) comprises one or more methods selected from the group consisting of: detection of restriction fragment length polymorphisms; detection of variable number of tandem repeat sequences; detection of dinucleotide repeat sequences; detection of short tandem repeat sequences; single-strand conformational polymorphism analysis; denaturing gradient gel electrophoresis; mismatch cleavage analysis by enzymatic or chemical means; polymerase chain reaction; rhesus blood group typing; primed in-situ labeling; in-situ hybridization; fluorescence in situ hybridization; multiplex polymerase chain reaction; and DNA sequencing.

19. The method of claim 1, wherein said screening said one or more cells for a desired genetic makeup in step (iii) comprises detecting the presence or absence of a specific DNA associated with a phenotype, disease or condition.

20. The method of claim 1, wherein said screening said one or more cells for a desired genetic makeup in step (iii) comprises in situ hybridization, polymerase chain reaction, nested polymerase chain reaction, fluorometric detection methods, restriction fragment length polymorphisms (RFLP) analysis, variable number of tandem repeat (VNTR) detection methods, short tandem repeat (STR) detection methods, single-strand conformational polymorphism (SSCP) analysis, denoting gradient gel electrophoresis (DGGE), and mismatch cleavage analysis.

* * * * *